United States Patent [19]

Scott et al.

[11] 3,976,675

[45] Aug. 24, 1976

[54] SILICATE-BASED SURFACTANT COMPOSITION

[75] Inventors: Robert N. Scott, Wallingford; Henry F. Lederle, North Haven; Frank J. Milnes, Guilford; Maurice A. Raymond, Northford, all of Conn.

[73] Assignee: Olin Corporation, New Haven, Conn.

[22] Filed: Nov. 19, 1974

[21] Appl. No.: 525,068

Related U.S. Application Data

[63] Continuation-in-part of Ser. No. 428,488, Dec. 26, 1973, abandoned.

[52] U.S. Cl. .................. 260/448.8 R; 260/2.5 AH
[51] Int. Cl.² ............................................. C07F 7/18
[58] Field of Search .......................... 260/448.8 R

[56] References Cited
UNITED STATES PATENTS

| | | | |
|---|---|---|---|
| 2,756,212 | 7/1956 | Hotten | 260/448.8 R X |
| 2,776,307 | 1/1957 | Abbott et al. | 260/448.8 R |
| 2,839,558 | 6/1958 | Kirkpatrick et al. | 260/448.8 R |
| 2,990,377 | 6/1961 | May | 260/448.8 R X |
| 2,993,871 | 7/1961 | Shannon et al. | 260/448.8 R X |
| 3,032,439 | 5/1962 | Müller et al. | 260/448.8 R X |
| 3,308,149 | 3/1967 | Schenk | 260/448.8 R |
| 3,509,192 | 4/1970 | Niederprüm et al. | 260/448.8 R |

*Primary Examiner*—Paul F. Shaver
*Attorney, Agent, or Firm*—Kenneth P. Glynn; F. A. Iskander

[57] ABSTRACT

A novel silicate-based surfactant composition is prepared by a selective process involving (1) reaction of silicon tetrahalide with water and alcohol followed by (2) transesterification with a polyether alcohol. The resulting surfactant composition is utilized as a stabilizer in the production of polyurethane foam.

17 Claims, No Drawings

SILICATE-BASED SURFACTANT COMPOSITION

This application is a continuation-in-part of copending application Ser. No. 428,488, filed Dec. 26, 1973 now abandoned.

This invention relates to the preparation of a novel silicate-based surfactant composition and to the use of this composition in the production of polyurethane foam.

It is know in the art that the silicone oils and soaps are of utility in the production of polyurethane foam. See for example R.J. Boudreau, *Modern Plastics*, January 1967. Various silicates and polyglycol silicates have also been disclosed in the chemical art. For example, a group of alkyl silicates is described in an article by Schwartz and Kessler, Z. Anorg. Chem. 236, 15; and polyglycol silicates are described in U.S. Pat. No. 2,630,446, U.S. Pat. No. 2,776,307 and U.S. Pat. No. 2,839,558. However, the utility of silicate-based surfactants in the production of polyurethane foam has not been taught by the prior art.

Now according to the invention a novel silicate-based surfactant composition has been found which is particularly useful as a stabilizer in the preparation of polyurethane foam. This novel composition is comprised of a combination of several silicate-based components, and it is prepared by a selective process which comprises:

a. reacting together silicon tetrahalide, an alcohol and water to form a reaction product made up of a volatile portion and a non-volatile portion, and b. catalytically transesterifying the non-volatile portion of the product of step (a) with a select polyether alcohol.

More in detail, the first step which is used in preparing the surfactant composition of the invention involves three essential reactants. The first of these is silicone tetrahalide in which the halogen is preferably chloride, bromine, iodine or a mixture thereof. Illustrative are silicone tetrachloride, silicon tetrabromide and silicon tetraiodide, the silicone tetrachloride being especially preferred.

The other two reactants are an alcohol and water. The former may be represented by the formula $R_1OH$ wherein $R_1$ is alkyl of 2-20, and preferably 2-10, carbon atoms or aryl of 6-14, and preferably 6-12, carbon atoms. Illustrative such alcohols include:

ethanol
propanol
butanol
pentanol
hexanol
heptanol
octanol
nonanol
decanol
dedecanol
octadecanol
eicosanol
phenol
toluol
xylenol
naphthol
ethyl phenol
benzyl alcohol
diphenyl carbinol It is particularly preferred to employ, as the alcohol reactant, an alkyl alcohol (i.e., $R_1$ = alkyl), the most preferred alkyl alcohols being those in which the alkyl group contains 3–8 carbons such as the propyl, butyl, pentyl, hexyl, heptyl and octyl alcohols.

The portions of alcohol reactant that is used may be varied over a wide range. For example a proportion of at least 1 mole may be used per mole of silicon tetrahalide, there being no critical upper limit. However, in order to prevent gel formation it is preferred to employ a proportion which is in excess of the stoichiometric amount that is required to react with the silicon tetrahalide and water. Such stoichiometric amount usually varies from about 1 to about 2 moles, per each mole of silicon tetrahalide, depending on the level of water that is used. It is further preferred not to employ too large a stoichiometric excess of alcohol in order to minimize the task of excess alcohol recovery and recycle. Thus pursuant to the preferred embodiments of the invention, a proportion of alcohol is used which ranges from about 2.0 to about 12, and more preferably about 3–10 moles per mole of silicon tetrahalide.

In effecting the reaction of step (a), the level of water is critical. Thus this level must not be less than about 0.2 nor more than about 2.0 moles per each mole of silicon tetrahalide. For optimum results, it is preferred to employ about 0.4–1.7, and still more preferably about 0.6–1.5, moles of water per each mole of silicon tetrahalide.

The reaction of the silicon tetrahalide, water and alcohol may be carried out at any suitable temperature which will bring about inter-reaction of these materials. Usually, however, elevated temperatures are used such as about 40°–200°C, preferably about 55°–110°C, and more preferably about 60°–100°C.

The pressure under which the reaction is effected is not critical. Thus any suitable pressure may be employed. Usually, where the reaction is conducted in an open vessel, atmospheric pressure is preferred for convenience and cost economy. However, lower as well as higher pressures may be employed if desired. For example the use of super-atmospheric pressure may be desirable, when the reaction is effected at highly elevated temperatures, in order to control or prevent boil-up of the reactants.

Any order of mixing the three reactants together may be used provided that the water is not brought in contact with the silicon tetrahalide in the absence of the alcohol. Thus for example the alcohol may be first mixed with the silicon tetrahalide, the water being then added to the mixture; or, alternatively and in accordance with the preferred embodiments of the invention, the water is first mixed with the alcohol and the mixture is then brought together with the silicon tetrahalide. During the time that the reactants are first brought together, cooling is preferably employed in order to prevent reactants boil-up upon initial contact. For example, a temperature below about 25°C, such as about −40°C to about 20°C, is employed. Thereafter, the mixed reactants are heated, preferably under reflux, to the desired temperature within the above-indicated range, in order to promote reaction which is usually completed in about 3–10 hours. A reaction product is then obtained which is made up of a volatile portion and a non-volatile portion. The components of the volatile portion, all of which have a boiling point no greater than about 125°C. at 10 m.m. of mercury pressure, are essentially by-product hydrohalic acid and unreacted or excess alcohol. The non-volatile portion, all the components of which have a boiling point above about 125°C. at 10 m.m. of mercury pressure, is a mixture comprised of various silicate-based components. The latter, which usually vary in number, molecular weight and molecular structure depending on the level of water and the level and identity of the alcohol used in effecting the reaction, are believed to include linear and branched silicate-based monomers, dimers, trimers, tetramers, and pentamers; cyclic tri-, tetra-, penta- and higher silicates; and fused-ring silicate-based systems. The non-volatile portion of the reaction product also contains varying proportions of unidentified silicon-containing materials including distillable and non-distillable fractions.

The second step in the process of the invention is the transesterification of the non-volatile portion of step (a). Before effecting the transesterification, it is preferred to separate or recover the non-volatile portion from the volatile portion. This is achieved for example by removing the volatile portion by any suitable or conventional method. Illustratively removal of the volatile portion may be effected by conventional stripping such as at a temperature of about 80°–120°C and reduced pressure, e.g., about 2–30 millimeters of mercury. Also if desired, further distillation of the product of step (a) may be carried out, before proceeding with the transesterification reaction, in order to remove low-molecular-weight silicates from the non-volatile portion.

Transesterification of the non-volatile portion is carried out by reaction with a select polyether alcohol. In accordance with the invention, this polyether alcohol is characterized by a molecular weight of about 500–5,000 and is represented by the formula $R_2\!-\!(C_nH_{2n}O)\!-\!H$ wherein $R_2$ is alkyl of 1–10 carbon atoms and the moiety $-(C_nH_{2n}O)-$ represents a polyoxyalkylene chain having from about 10 to 100% by weight of oxyethylene units and, correspondingly, from about 90 to 0% of oxypropylene units, oxybutylene units or a mixture of oxypropylene and oxybutylene units. Such a polyether alcohol can be prepared by methods well known in the art wherein, for example, an alkyl alcohol is condensed, in the presence of a basic catalyst such as KOH, with ethylene oxide or with a mixture of ethylene oxide and higher alkylene oxides as specified above using random or step-wise addition.

The preferred polyethers for use in the transesterification reaction are those having a molecular weight of about 1,000–4,000. Particularly preferred polyethers are those represented by the formula above wherein $R_2$ contains 1–6 carbons, e.g., methyl, ethyl, propyl, butyl, heptyl or hexyl, and the moiety $-(C_nH_{2n}O)-$ represents a polyoxyethylene chain or a polyoxyethylene-oxypropylene chain having a weight ratio of oxyethylene to oxypropylene units ranging from about 1:2 to about 2:1.

In carrying out the transesterification reaction, the polyether alcohol represented by the above formula is employed in a molar proportion which is sufficient to bring about replacement of part, but not all, of the alkoxy or aryloxy moieties, i.e., $R_1O-$, in the silicate-based intermediate mixture prepared in step (a) with polyether alkoxy moieties, i.e., $R_2-(C_nH_{2n}O)-$. This porportion ranges from about 0.006 to about 1.1 of moles of polyether alcohol per each mole of silicon tetrahalide used in step (a), provided that it does not exceed about 55% of the molar proportion of alcohol $R_1OH$ consumed in the reaction of step (a). A preferred molar proportion of polyether alcohol to be used in the transesterification reaction ranges from about 0.06 to about 0.8 mole per each mole of silicone tetrahalide used in step (a), such a proportion further being no less than about 3% nor more than about 49% of the molar proportion of alcohol consumed in step (a).

The reaction is effected in the presence of a transesterification catalyst. Any such catalyst may be employed which is effective in promoting the reaction. This includes a wide variety of basic and acidic catalysts. The basic catlaysts are exemplified by the alkylamines, the alkali metals (e.g., Na, K, Li, Cs, Ru), the alkaline earth metals (e.g., Ca, Mg, Ba, Sr), and the hydrides, alkoxides and hydroxides of the alkali and alkaline earth metals. The acidic catalysts include the Lewis acids as described for example in Jack Hine, *Physical Organic Chemistry*, 1962, McGraw-Hill Book Co., N.Y., the entire disclosure of which is incorporated herein by reference. Exemplificative such acids include boron trifluoride and its etherate derivatives, ferric chloride, ferrous chloride, stannic chloride, titanium tetrachloride, antimony pentachloride, aluminum chloride, hydrogen fluoride, aluminum bromide, triethyl aluminum, zinc chloride, zinc bromide, tetrabutyl titanate, and so forth. In accordance with the preferred embodiments of the invention, a transesterification catalyst is employed which is selected from a Lewis acid, an alkali metal and an alkali metal hydride, the alkali metals and their hydrides (e.g., sodium and potassium hydride) being especially preferred.

The transesterification is effected at elevated temperatures. For example a temperature ranging from about 65° to about 320°C, preferably about 80°–260°C, and more preferably about 120°–220°C is used. The reaction pressure is not critical, but atmospheric pressure is preferred for economy and simplicity of operation. It is also preferred to effect the reaction in the substantial absence of moisture. To this end for example, a blanket or atmosphere of nitrogen or other inert gas may be used. Complete reaction time usually varies from about 1 to about 10 hours depending on the reaction temperature that is used.

By virtue of the partial replacement of alkoxy or aryloxy moieties with polyether alkoxy moieties which is effected in the transesterification reaction, some of the alcohol consumed in step (a) will be liberated during transesterification. Thus the product of the transesterification reaction will be comprised of a proportion of alcohol $R_1OH$, which proportion varies depending on the molar proportion of polyether alcohol used in transesterification, and a mixture comprised of several silicate-based species which make up the essential components of the surfactant composition of the invention. The entire transesterification product, including liberated alcohol, may be used as is in the production of polyurethane foam. However, it is preferred to remove the liberated alcohol before utilizing the transesterification product. Such removal may be achieved by any suitable or conventional method such as distillation. The removal of liberated alcohol, furthermore, may be carried out or commenced during transesterification or after the transesterification reaction is completed. Thus it is to be understood that the language used in the specification and claims herein in connection with the removal of liberated alcohol is intended to encompass initiating such removal during and/or after transesterification.

The surfactant composition which is recovered after removal of liberated alcohol is a viscous liquid mixture comprised of several structurally unidentified, high boiling sililcate-based species which are believed to have an average molecular weight within the range of about 700–7,000. The silicate-based surfactant composition of the invention is further characterized by an over-all silicon content ranging from about 5 to about 23% by weight, and, correspondingly, an over-all carbon content ranging from about 72 to about 23% and an over-all hydrogen content from about 12 to about 6%, the balance being mainly oxygen. The preferred ranges of these components are about 6–10% of silicon and correspondingly about 65–40% of carbon and about 10–7% of hydrogen.

In accordance with the most preferred embodiment of the invention, a silicate-based surfactant composition is prepared by a process which comprises the following steps:

A. Preparation of a mixture of silicon tetracholoride and, per every mole of the silicon tetrachloride, about 0.7–1.4 moles of water and about 3–8 moles of an alcohol selected from isopropyl alcohol and secondary butyl alcohol. This step is carried out at a reduced temperature such as from about −30°C to about 20°C and it is preferably effected by gradually adding a mixture of water and alcohol to the silicon tetrachloride.

B. Reaction of the mixture prepared in step A. Such reaction is effected at a temperature of about 60°–100°C and under reflux conditions, the product of the reaction being made up of hydrochloric acid, excess unreacted alcohol and a non-volatile mixture comprised of silicate-based materials.

C. Recovery of the non-volatile mixture obtained in step B. Such recovery may be achieved by stripping off the hydrochloric acid and excess unreacted alcohol preferably using a temperature of about 80°–120° and a pressure of 2–30 millimeters of mercury.

D. Catalytic transesterification of the non-volatile mixture obtained in step C with a polyether alcohol having a molecular weight of about 1,200–2,500 and represented by the formula $C_4H_9$ $+C_nH_{2n}O+$ H in which the moiety $+C_nH_{2n}O+$ represents a polyoxyethylene-oxypropylene chain having a weight ratio of oxyethylene to oxypropylene units ranging from about 4:6 to about 6:4. In carrying out this step, a proportion of the polyether alcohol is used which ranges from about 0.1 to about 0.7 mole per each moles of silicon tetrachloride used in step A. Furthermore, the transesterification reaction is effected at a temperature of about 140°–220 °C and in the substantial absence of moisture such as by using a blanket or atmosphere of nitrogen gas. The transesterification catalyst is a Lewis acid, an alkali metal or an alkali metal hydride, the alkali metals and their hydrides being especially preferred such as sodium, sodium hydride, potassium and potassium hydride. Along with the silicate-based surfactant composition of the invention, the transesterification product will comprise some liberated alcohol.

E. Recovery of the silicate-based surfactant composition obtained in step D. Such recovery is achieved by removing the liberated alcohol such as by distilling it off.

The surfactant composition of the invention is of particular utility as a stabilizer in the production of polyurethane foam. As such, it constitutes an economically attractive and valuable substitute for prior art silicone surfactants which are costlier or more difficult to prepare.

Pursuant to this invention, polyurethane foam is prepared from a foam forming reaction mixture containing the silicate-based surfactant composition described above. In preparing the polyurethane foam, either the so-called "one-shot method" or the "prepolymer technique" may be employed. Any combination of polyols, including polyether polyols and polyester polyols, organic polyisocyanate, foaming agent, catalyst and other reactants capable of forming a polyurethane foam can be employed. Typical formulations are described in U.S. Pat. No. 3,072,582, issued Jan. 8, 1963, and Canadian Patent No. 705,938, issued Mar. 16, 1965.

While, as indicated above, both polyether and polyester polyols can be employed in preparing the foam, the polyether polyols are preferred. Any suitable polyether polyols may be used for this purpose. These polyether polyols usually have a hydroxyl number for example from about 25 to about 800.

The polyether polyols include for example oxyalkylated polyhydric alcohols having a molecular weight range of about 200–10,000 and preferably between about 250–8,000. These oxyalkylated polyhydric alcohols are generally prepared by methods well known in the art such as by reacting, in the presence of an alkaline catalyst, a polyhydric alcohol and an alkylene oxide such as ethylene oxide, propylene oxide, butylene oxide, amylene oxide, epichlorohydrin, and mixtures of these alkylene oxides, using either random or step-wise addition.

Polyhydric alcohols suitable for use in preparing the polyether polyols include for example ethylene glycol, propylene glycol, 2,3-butylene glycol, 1,3-butylene glycol, 1,5-pentane diol, 1,6-hexane diol, glycerol, trimethylolpropane, sorbitol, pentaerytyritol, methyl glucoside, sucrose, dextrose, mixtures thereof and the like. If desired, a portion or all of the polyhydric alcohol may be replaced with another compound having at least two reactive hydrogen atoms, such as the alkyl amines, the alkylene polyamines, the cyclic amines, the amides, and the polycarboxylic acids. Suitable alkyl amines and alkylene polyamines include methylamine, ethylamine, propylamine, butylamine, hexylamine, ethylenediamine, 1,6-hexanediamine, diethylenetriamine, and the like. The cyclic amines are exemplified by piperazine, 2-methylpiperazine and 2,5-dimethylpiperazine; the aides are exemplified by acetamide, succinamide and benzenesulfonamide, and illustrative polycarboxylic acids include adipic acid, succinic acid, glutaric acid, anonotic acid, diglycollic acid, and the like.

The organic polyisocyanates used in the preparation of the polyurethane foams include, for example, toluene diisocynate, such as the 80:20 and the 65:35 mixture of the 2,4-and 2,6-isomers, ethylene diisocyanate, proplyene diisocyanate, methylene-bis-4-phenyl isocyaate, 3,3'-bitoluene-4,4'-di-isocyanate, hexamethylene diisocyanate, naphthalene-1,5-di-isocyanate, polymethylene polyphenylisocyanate, mixtures thereof and the like. The preferred organic polyisocyanate is toluene diisocyanate. The amount of isocyanate employed in the process of this invention should be sufficient to provide at least about 0.7, and preferably about 0.9–1.20, NCO groups per hydroxyl group present in the reaction system.

The polyurethane foams are prepared in the presence of a foaming agent which may be any of those known to be useful for this purpose. Illustrative are water and organic foaming agents containing up to about seven carbon atoms such as the halogenated hydrocarbons, lower molecular weight alkanes, ethers, and mixtures thereof. Typical halogenated hydrocarbons include, but are not limited to, monofluorotrichloromethane, dichlorofluoromethane, difluorodichloromethane, 1,1,2-trichloro-1,2,2-trifluoroethane, dichlorotetrafluoroethane, ethyl chloride, methylene chloride, chloroform, and carbon tetrachloride. Other useful foaming agents include lower molecular weight alkanes, alkenes and ethers such as methane, ethane, ethylene, propane, propylene, pentane, hexane, heptane, ethyl ether, diisopropyl ether, mixtures thereof, and the like. The amount of foaming agent employed may be varied within a wide range. Generally, however, the halogenated hydrocarbons are employed in an amount from about 1 to about 50, and preferably about 5–35, parts per 100 parts by weight of the polyol, and generally water is employed in an amount from about 1.0 to about 6.0 parts by weight per 100 parts by weight of the polyol.

The polyurethane foams are prepared in the presence of a catalytic amount of a reaction catalyst. The catalyst employed may be any of the catalysts known to be useful for this purpose, such as tertiary amines and metallic salts, particularly stannous salts, and mixtures thereof. Typical tertiary amines include, but are not limited to, N-ethyl morpholine, N-hydroxyethyl morpholine, triethylene diamine, triethylamine and trimethylamine. Typical metallic salts include, for example, the salts of antimony, tin and iron, e.g., dibutyltin diluarate, stannous octoate, and the like. Any catalytic proportion of catalyst or catalyst mixture may be employed such as from about 0.1 to about 3.0 percent, and preferably from about 0.5 to about 2.5 percent, by weight of the polyol.

In preparing polyurethane foams in accordance with this invention, any suitable proportion of silicate-based surfactant composition described above may be used which is effective in stabilizing the foam and providing other desirable cell and foam characteristics without otherwise interfering with the foaming reaction or materially altering the properties of the resulting foam. For example, from about 0.01 to about 5 parts by weight of surfactant are employed per 100 parts of polyol. Preferably, the amount of surfactant used is from about 0.25 to about 3 parts by weight per 100 parts of polyol.

Various additives may also be included in the foam forming reaction mixture which serve to provide different properties in the polyurethane foam. For example, filters such as clay, calcium sulfate, or ammonium phosphate may be added to lower cost and improve physical properties. Ingredients such as dyes may be added for color, and fibrous glass, asbestos, or synthetic fibers may be added for strength. In addition, plasticizers, deodorants, antioxidants and flame retardants may be added.

In the practice of this invention, a polyurethane foam-forming reaction mixture comprising the above-described ingredients is fed to a suitable reaction zone such as by pouring into a suitable mold or onto a moving conveyor belt where reaction proceeds. The foaming reaction is exothermic, and auxiliary heat is usually not necessary to effect the reaction, although it may be employed. After the reactants have been admixed for a period of between about 0.1 and about 20 seconds, an emulsion or "cream" forms. As the temperature increases from the reaction, gas bubbles are generated bringing about the formation of an uncured cellular gel material which usually cures fairly rapidly at room temperature. Once cured, the foam will be ready for use in various cushioning and inculating applications.

The following examples are provided to illustrate the invention. All parts and percentages given in these examples are by weight unless otherwise specified.

EXAMPLE 1

A 5 liter 3-neck flask fitted with a magnetic stirrer, a thermometer and a gas outlet was charged with 849.5 grams (5 moles) of silicon tetrachloride and cooled to 0°C with an ice-water bath. A solution of 81 mls. (4.5 moles) of $H_2O$ in 2 kgs. (33.3 moles) of isopropanol was then added with stirring over a period of 2.5 hours. Rapid HCl evolution during the early stages of the aqueous isopropanol addition helped to cool the reaction mixture making it relatively easy to maintain a temperature between 4° and 10°C. After about half the isopropanol was added, HCl evolution slowed considerably resulting in an apparent exotherm, and frequent stirring of the ice bath was required to maintain the temperature of the reaction mixture below 20°C. During the latter stages of the addition, the reaction mixture became cloudy with ultimate formation of two phases. After addition of aqueous isopropanol was complete, the mixture was heated to 82°C under reflux for 3 hours, at which point it was homogeneous.

The product thus formed was then stripped of volatiles up to a bottoms temperature of 100°C and 20 m.m. of mercury pressure. The over-head fractions, mainly excess unreacted isopropanol and by-product hydrocyloric acid, were discarded, leaving a viscous liquid residual intermediate weighing 662 grams and having a viscosity of 60 c.s. at 100°F.

The amount of 215 grams of the intermediate prepared above was used to prepare a silicate-based surfactant composition following this procedure. A 1-liter, 3-neck flask equipped with a mechanical stirrer, a nitrogen inlet, a dry ice-cooled Dewar condenser and a Dean-Stark trap was charged with 350 g of a butanol initiated, oxyethylated, oxypropylated polyether having a molecular weight of 1,800 and a 1:1 weight ratio of ethylene oxide: propylene oxide. To this there was added 215 grams of the intermediate obtained above and 0.3 gram of tetrabutyl titanate catalyst. The flask was then immersed in a 130°C oil bath. With a nitrogen sweep of 550 cc/min. and rapid stirring (375 rpm), the oil bath was rapidly heated (10–15 min.) to 195°C and maintained at this temperature for 4 hours. The product was cooled under nitrogen and the volatile distillate (15 g. isopropanol) was discarded leaving a final product of 524 grams which was a homogeneous liquid surfactant composition having a kinematic viscosity of 407 cs. at 100°F. The components of this composition could not be identified by available methods, e.g., gas chromatography, mass spectrometry, nuclear magnetic resonance, and infrared analysis. However, its over-all content of silicon, carbon, hydrogen and oxygen was determined by gravimetric analysis to be as follows:

silicon: 7.25%
carbon: 50.24%
hydrogen: 8.8% oxygen: 33.7%

A flexible polyurethane foam was prepared from a reaction mixture comprised 1.5 mls. of the surfactant composition prepared above and the following ingredients.

| Ingredients | Amounts |
| --- | --- |
| Polyether polyol [1] | 100 g. |
| Toluene diisocyanate [2] | 42 ml. |
| Water | 4 ml. |
| Catalyst System | |
| a) triethylene diamine [3] | 0.3 ml. |
| b) stannous octoate | 0.25 ml. |

[1] This is a 3,000 molecular weight polyether triol prepared by oxypropylation of glycerin.
[2] This is a 4/1 mixture of the 2,4- and 2,6-isomers of toluene diisocyanate.
[3] This is a commercially obtained product sold under the trademark "Dabco 33LV" and consisting mainly of 1/3 triethylene diamine and 2/3 dipropylene glycol.

The above mixture was hand mixed at room temperature and immediately poured into a cake box mold at room temperature. Using a stop-watch, the "cream time", "rise time", and "gel time" were mesured, all being from the moment the mixture was placed into the mold. The "cream time" is the time elapsed, up to the point when foaming commences, during which time the mixture is transformed from a liquid to a cream or emulsion. The "rise time" is the time elapsed for completion of the foaming reaction or expansion of the foam. This is usually evidenced by the appearance of gas bubbles on the surface of the foam. The "gel time" is the time elapsed for the resulting foam to become a self-supporting body as evidenced by the foam exhibiting resistance to being penetrated by a dull instrument. The results of these time measurements are summarized in Table I below.

Table I

| | Foaming Data | | |
| --- | --- | --- | --- |
| Run | Cream Time (sec.) | Rise Time (sec.) | Gel Time (sec.) |
| 1 | 10 | 70 | 133 |
| 2 | 8 | 62 | 107 |
| 3 | 8 | 60 | 108 |

On visual examination, the foam had a regular or uniform cell structure (approximately 53 cells/sq. inch). Its air permeability (3.96 cubic feet/minute), measured before and after flexing according to the test described is ASTM D-1564, indicated a desirable open celled structure.

EXAMPLES 2–15

Fourteen additional surfactant compositions were prepared using the general procedure of Example 1 with the following variations. First the degree of stripping the product of the reaction of silicon tetrachloride, water and isopropanol was varied such as to achieve an intermediate having differing viscosities. Secondly, the proportions of this intermediate used in the transesterification reaction was varied in each of Examples 2–15. Thirdly different molecular weight polyethers were used in the transesterification reaction and at varying levels. Details of Examples 2–15 are provided in Table II below.

TABLE II

| Example No. | Intermediate used in Transesterification | | Polyether Used in Transesterification | | Surfactant Product | | |
| --- | --- | --- | --- | --- | --- | --- | --- |
| | Viscosity (cs at 100°F) | Weight used (gms.) | Mol. Wt. | Weight Used (gms.) | Yield (gms) | Appearance | Viscosity (cs at 100°C) |
| 2 | 43.8 | 32 | 1,800 | 68 | 97.8 | opalescent | 429 |
| 3 | 43.8 | 19 | 1,800 | 81 | 97.5 | opalescent | 658 |
| 4 | 82.8 | 67 | 1,800 | 33 | 96.7 | clear | 335 |
| 5 | 82.8 | 80 | 1,800 | 20 | 95.9 | clear | 654 |
| 6 | 159.0 | 53 | 1,800 | 47 | 98.4 | hazy | 359 |
| 7 | 159.0 | 37 | 1,800 | 63 | 97.8 | opalescent | 500 |
| 8 | 159.0 | 22 | 1,800 | 78 | 98.1 | opalescent | 582 |
| 9 | 362.9 | 38 | 1,800 | 62 | 97.4 | clear | 787 |
| 10 | 362.9 | 23 | 1,800 | 77 | 97.8 | clear | 782 |
| 11 | 121.9 | 38 | 966 | 62 | 96.4 | clear | 221 |
| 12 | 121.9 | 38 | 1,250 | 62 | 97.1 | opalescent | 327 |
| 13 | 121.9 | 38 | 3,000 | 62 | 97.8 | opaque | 1,161 |
| 14 | 121.9 | 38 | 4,000 | 62 | 97.5 | opaque | paste |
| 15 | 68.7 | 38 | 3,000 | 62 | 97.5 | opalescent | 687 |

EXAMPLE 16

The exact procedure of Example 1 was followed with one exception. This is that the intermediate product obtained by the reaction of carbon tetrachloride with water and isopropanol was subjected to further purification by distillation. To this end, it was placed in a 1-liter, 3-neck flask equipped with a magnetic stirrer, a 5 inch vacuum jacketed Virgreux column, a vacuum take-off head, a fraction cutter, and an immersed pot thermometer. Distillation was carried out up to a bottoms temperature of 210°C and 15 m.m. of mercury pressure. The bottoms fraction thus obtained weighed 538 grams which represented 75% yield based on SiCl₄ charged. This fraction which has a kinematic viscosity at 100°F of 139.0 cs was then transesterified exactly as described in Example 1. After removal of liberated isopropanol, a liquid surfactant composition was obtained which has a viscosity of about 390 cs at 100°F. The over-all silicon, carbon, hydrogen and oxygen content in this composition was determined by gravimetric analysis to be as follows: 7.94% silicon, 50.56% carbon, 9.03% hydrogen and 32.47% oxygen.

The product of this example was found to be effective as a stabilizer, when used exactly as described in Example 1, in the preparation of polyurethane foam.

EXAMPLE 17

The identical procedure of Example 16 was followed with the following exceptions. In carrying out the transesterification reaction, 62 grams of the butanol-initiated polyether and 38 grams of the bottoms fraction, of the product of the reaction of SiCl₄ with water and isopropyl alcohol, were used. In addition, the catalyst used to promote transesterification was metallic sodium (0.05 gram) instead of the tetrabutyl titanate. Finally the transesterification reaction was effected at 165°C.

After transesterification and removal of evolved isopropanol, a homogeneous, viscous liquid product was obtained which weighed 96 grams. This product was found to be equally effective as a stabilizer when used, exactly as described in Example 16, in the preparation of polyurethane foam.

EXAMPLE 18

The identical procedure of Example 17 was followed except that 0.05 gram of sodium hydride was used as the transesterification catalyst instead of the metallic sodium. Again the product of transesterification, after removal of liberated isopropanol, was found to be an effective stabilizer in the production of polyurethan foam.

EXAMPLE 19

The identical procedure of Example 17 was followed with one exception. This is that in carrying out the first reaction, instead of 33.3 moles, 20 moles of isopropanol were used. The final product, after being freed of liberated isopropanol, was found to be an effective stabilizer in polyurethane foam production.

EXAMPLE 20

The procedure of Example 19 was followed except that instead of the 20 moles of isopropanol used in the first reaction, 33 moles of butanol-2 were employed. The final product, after removal of liberated butanol, was a viscous liquid. Its over-all content of silicon, carbon, hydrogen and oxygen was determined by gravimetric analysis to be as follows:

silicon: 7.58%
carbon: 54.14%
hydrogen: 9.49%
oxygen: 28.79%

The product of this example was found to be an effective stabilizer in the production of polyurethane foam.

EXAMPLES 21–22

Two silicate-based surfactant compositions were prepared following the procedure of Example 17 with one exception. This is that in carrying out the first reaction, instead of using 0.9 moles of water per each mole of silicon tetrachloride, 0.4 mole was used in Example 21 and 1.3 moles were used in Example 22.

What is claimed is:
1. A process for preparing a silicate-based surfactant composition which comprises:
   a. reacting together, at a temperature of about 40°–200°C, (1) a silicon tetrahalide selected from the group consisting of silicon tetrachloride, silicon tetrabromide, and silicon tetraiodide, and, per every mole of said silicon tetrahalide (2) about 0.2–2.0 moles of water and (3) at least about one mole of an alcohol represented by the formula $R_1OH$ wherein $R_1$ is alkyl of 2–20 carbon atoms or aryl of 6–14 carbon atoms, the reaction yielding a product made up of a volatile portion and a non-volatile portion, and
   b. at a temperature of about 65°–320°C and in the presence of a transesterification catalyst, reacting the non-volatile portion of the product of step (a) with a polyether alcohol having a molecular weight of about 500–5,000 and represented by the formula $R_2$-(-$C_nH_{2n}O$-)- H wherein $R_2$ is alkyl of 1–10 carbon atoms and the moiety -(-$C_nH_{2n}O$-)- represents a polyoxyalkylene chain consisting of from about 10 to 100 percent by weight of oxyethylene units, and, correspondingly, about 90–0 percent of oxypropylene units, oxybutylene units or a mixture of oxypropylene and oxybutylene units, said polyether alcohol being employed in a molar proportion ranging from about 0.006 to about 1.1 moles per every mole of said silicon tetrayalide which is used in step (a), with the proviso that the molar proportion of said polyether alcohol is no more than about 55% of the molar proportion of alcohol consumed in the reaction of step (a).

2. A surfactant composition prepared by the process of claim 1.

3. A process as claimed in claim 1 which includes the intermediate step of removing said volatile portion before reacting said non-volatile portion of the product of step (a) with said polyether alcohol.

4. The process of claim 3 wherein said transesterification catalyst is selected from the group consisting of a Lewis acid, an alkali metal, an alkali metal hydride, an alkaline earth metal, and an alkaline earth metal hydride.

5. The process of claim 4 wherein said $R_1$ is alkyl of 2–10 carbon atoms.

6. A surfactant composition prepared by the process of claim 5.

7. The process of claim 5 wherein the reaction of step (b) is carried out in the substantial absence of moisture.

8. A process as claimed in claim 7 which includes the added step of removing alcohol of said formula $R_1OH$ which is liberated during the reaction of step (b).

9. A surfactant composition prepared by the process of claim 8.

10. The process of claim 8 wherein said silicon tetrahalide is silicate tetrachloride.

11. The process of claim 10 wherein said polyether alcohol has a molecular weight of about 1,500–4,000 and in which said $R_2$ is alkyl of 1–6 carbon atoms and said -(-$C_nH_{2n}O$-)- moiety represents a polyoxethylene chain or a polyoxyethylene-oxypropylene chain having a weight ratio of oxyethylene to oxypropylene units ranging from about 2:1 to about 1:2.

12. A surfactant composition prepared by the process of claim 11.

13. The process of claim 11 wherein the reaction of step (a) is carried out at about 55°–110°C, under reflux and using, per every mole of said silicon tetrachloride, about 2–12 moles of said alcohol and about 0.4–1.7 moles of said water.

14. The process of claim 13 wherein the reaction of step (b) is carried out at about 80°–260°C and using about 0.06 –0.8 moles of said polyether alcohol per each mole of said silicon tetrachloride which is used in step (a).

15. A surfactant composition prepared by the process of claim 14.

16. A process for preparing a silicate-based surfactant composition which comprises the following steps:

a. at a temperature from about −30°C to about 20°C, mixing together silicon tetrachloride and, per every mole of said silicon tetrachloride, about 0.7–1.4 moles of water and about 3–8 moles of isopropyl alcohol, b. allowing said mixture to react at a temperature of about 60°–100°C and under reflux conditions, thereby forming a reaction product made up of hydrochloric acid, unreacted isopropyl alcohol and a non-volatile mixture comprised of silicate-based materials, c. stripping off said hydrochloric acid and unreacted isopropyl alcohol, d. reacting said non-volatile mixture with a polyether alcohol having a molecular weight of about 1,200–1,500 and represented by the formula $C_4H_9$ $+C_nH_{2n}O+$ H wherein the moiety $+C_nH_{2n}O+$ represents a polyoxyethylene-oxypropylene chain having a weight ratio, of oxyethylene to oxypropylene units, ranging from about 6:4 to about 4:6, the reaction being carried out;

1. using about 0.1–0.7 mole of said polyether alcohol per each mole of said silicon tetrachloride used in step (a), 2. at a temperature of about 140°–220°C, 3. in the substantial absence of moisture, and 4. in the presence of a transesterification catalyst selected from the group consisting of a Lewis acid, an alkali metal and an alkali metal hydride, thereby forming a product comprised of a silicate-based surfactant composition and liberated isopropyl alcohol, and e. removing said liberated isopropyl alcohol and recovering said silicate-based surfactant composition.

17. A surfactant composition prepared by the process of claim 16.

* * * * *